US00PP18514P2

(12) United States Plant Patent
Kientzler

(10) Patent No.: US PP18,514 P2
(45) Date of Patent: Feb. 26, 2008

(54) **NEW GUINEA *IMPATIENS* PLANT NAME 'KIE186'**

(50) Latin Name: *Impatiens hawkeri*
Varietal Denomination: KIE186

(75) Inventor: Ludwig Kientzler, Gensingen (DE)

(73) Assignee: The Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 11/518,599

(22) Filed: Sep. 8, 2006

(51) Int. Cl.
*A01H 5/00* (2006.01)

(52) U.S. Cl. ..... Plt./318

(58) Field of Classification Search ..... Plt./318
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of New Guinea *Impatiens* plant named 'KIE186', characterized by its upright, outwardly spreading and mounded plant habit; freely branching habit; dense and bushy growth habit; dark green and yellow green variegated leaves; freely flowering habit; and large light pink-colored flowers that are positioned above and beyond the foliage.

1 Drawing Sheet

Botanical designation: *Impatiens hawkeri.*
Cultivar denomination: 'KIE186'.

BACKGROUND OF THE INVENTION

The present invention relates to a new and distinct cultivar of New Guinea *Impatiens* plant, botanically known as *Impatiens hawkeri,* and hereinafter referred to by the name 'KIE186'.

The new *Impatiens* is a product of a planned breeding program conducted by the Inventor in Gensingen, Germany. The objective of the breeding program was to develop new *Impatiens* cultivars with numerous large flowers and attractive foliage and flower coloration.

The new *Impatiens* originated from a cross-pollination made by the Inventor in November, 2000, of a proprietary selection of *Impatiens hawkeri* identified as code number 00-113, not patented, as the female, or seed, parent with the *Impatiens hawkeri* cultivar Kidomia, disclosed in U.S. Plant Pat. No. 14,143, as the male, or pollen, parent. The cultivar KIE186 was discovered and selected by the Inventor as a flowering plant within the progeny of the stated cross-pollination in a controlled environment in Gensingen, Germany in April, 2001.

Asexual reproduction of the new cultivar by terminal cuttings propagated in a controlled environment in Gensingen, Germany since May, 2001 has shown that the unique features of this new *Impatiens* are stable and reproduced true to type in successive generations of asexual reproduction.

SUMMARY OF THE INVENTION

The cultivar KIE186 has not been observed under all possible environmental conditions. The phenotype may vary somewhat with variations in environment such as temperature and light intensity, without, however, any variance in genotype.

The following traits have been repeatedly observed and are determined to be the unique characteristics of 'KIE186'.

These characteristics in combination distinguish 'KIE186' as a new and distinct cultivar of New Guinea *Impatiens:*

1. Compact, upright, outwardly spreading and mounded plant habit.
2. Freely branching habit; dense and bushy growth habit.
3. Green and yellow green variegated leaves.
4. Freely flowering habit.
5. Large light pink-colored flowers that are positioned above and beyond the foliage.

In side-by-side comparisons conducted in Gensingen, Germany, plants of the new *Impatiens* differed from plants of the female parent selection in the following characteristics:

1. Plants of the new *Impatiens* had darker green-colored leaves than plants of the female parent selection.
2. Plants of the new *Impatiens* had larger flowers than plants of the female parent selection.

In side-by-side comparisons conducted in Gensingen, Germany, plants of the new *Impatiens* differed from plants of the male parent, the cultivar Kidomia, in the following characteristics:

1. Leaf variegation of plants of the new *Impatiens* was less pronounced than leaf variegation of plants of the cultivar Kidomia.
2. Plants of the new *Impatiens* had larger flowers than plants of the cultivar Kidomia.
3. Plants of the new *Impatiens* and the cultivar Kidomia differed in flower coloration.

Plants of the new *Impatiens* can be compared to plants of the New Guinea *Impatiens* cultivar Balcelbupi, disclosed in U.S. Plant Pat. No. 13,410. In side-by-side comparisons conducted in Gensingen, Germany, plants of the new *Impatiens* differed from plants of the cultivar Balcelbupi in the following characteristics:

1. Plants of the new *Impatiens* and the cultivar Balcelbupi differed in foliage color as plants of the cultivar Balcelbupi had dark green-colored foliage.

2. Plants of the new *Impatiens* and the cultivar Balcelbupi differed slightly in flower color.

BRIEF DESCRIPTION OF THE PHOTOGRAPHS

The accompanying photographs illustrate the overall appearance of the new *Impatiens*. The photographs show the colors as true as it is reasonably possible to obtain in colored reproductions of this type. Colors in the photographs may differ slightly from the color values cited in the detailed botanical description which accurately describe the colors of the new *Impatiens*.

The photograph at the bottom of the sheet comprises a side perspective view of a typical flowering plant of 'KIE186' grown in a container.

The photograph at the top of the sheet is a close-up view of a typical flower of 'KIE186'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Encinitas, Calif. during the winter and early spring in a polyethylene-covered greenhouse and under conditions and practices which approximate those generally used in commercial New Guinea *Impatiens* production. During the production of the plants, day temperatures averaged 24° C., night temperatures averaged 19° C. and light levels averaged 4,000 foot candles. Measurements and numerical values represent averages for typical flowering plants. Single plants were grown in one-gallon containers and were about 18 weeks old when the photographs and the detailed description were taken.

Botanical classification: *Impatiens hawkeri* cultivar KIE186.

Parentage:

*Female, or seed, parent.*—Proprietary selection of *Impatiens hawkeri* identified as code number 01-342, not patented.

*Male, or pollen parent.*—*Impatiens hawkeri* cultivar Kidomia, disclosed in U.S. Plant Pat. No. 14,143.

Propagation:

*Type.*—Vegetative cuttings.

*Time to initiate roots, summer.*—About 14 days at 23° C.

*Time to initiate roots, winter.*—About 17 days at 20° C.

*Time to produce a rooted young plant, summer.*—About 21 days at 23° C.

*Time to produce a rooted young plant, winter.*—About 24 days at 20° C.

*Root description.*—Fine, fibrous; white to brown in color.

*Rooting habit.*—Freely branching.

Plant description:

*Plant form.*—Compact, upright, outwardly spreading and mounded plant habit.

*Growth and branching habit.*—Vigorous and freely branching habit; about eleven to twelve lateral branches developing at the base; dense and bushy growth habit. Pinching, that is, removal of the terminal apices, is typically not required, but will enhance branching.

*Plant height.*—About 26 cm.

*Plant diameter or spread.*—About 46 cm.

*Lateral branches.*—Length: About 17 cm. Diameter: About 8 mm. Internode length: About 4.5 to 5.5 cm. Texture: Smooth, glabrous. Color: 184A.

Foliage description:

*Arrangement.*—Opposite or in whorls, simple.

*Length.*—About 11.5 cm.

*Width.*—About 3.4 cm.

*Shape.*—Elliptical.

*Apex.*—Acuminate.

*Base.*—Attenuate.

*Margin.*—Serrate with ciliation.

*Texture, upper and lower surfaces.*—Smooth, glabrous.

*Venation pattern.*—Pinnate.

*Color.*—Developing foliage, upper surface: 147A. Developing foliage, lower surface: 183A. Fully expanded foliage, upper surface: Towards the margins, 147A; towards the center, 146B; along midvein, 153C and close to 151D; venation, 184B. Fully expanded foliage, lower surface: Towards the margins, 183B; centers, 182B; venation, 185A.

*Petiole.*—Length: About 3.4 cm. Diameter: About 3 mm. Texture, upper and lower surfaces: Smooth, glabrous. Color, upper and lower surfaces: 184B.

Flower description:

*Flower type and flowering habit.*—Single axillary flowers. Freely flowering habit; usually about four to five open flowers and flower buds per lateral branch. Flowers positioned above the foliage and typically face upright or outward. Flowers last about one week under greenhouse conditions. Petals self-cleaning, gynoecium persistent. Flowers not fragrant.

*Natural flowering season.*—Year-round under greenhouse conditions. In the garden, flowering from spring until fall in Germany. Plants begin flowering about eight to twelve weeks after planting.

*Flower size.*—Length: About 5 cm. Width: About 5 cm. Depth: About 2.5 cm.

*Flower buds.*—Length: About 2.3 cm. Diameter: About 1.1 cm. Shape: Ovoid; pointed. Color: 74D.

*Petals.*—Quantity/arrangement: Five per flower in a single whorl. Length, banner petal: About 2.5 cm. Length, lateral petals: About 2.9 cm. Length, lower petals: About 2.7 cm. Width, banner petal: About 3.3 cm. Width, lateral petals: About 2.6 cm. Width, lower petals: About 3.2 cm. Shape: Cordate. Apex: Emarginate. Base: Acute. Margin: Entire. Texture, upper and lower surfaces: Smooth, glabrous. Color: When opening, upper surface: 73A to 73B to 73C, darkest towards the margins. When opening, lower surface: 73C to 73D. Fully opened, upper surface: 73B to 73C to 73D, darkest towards the margins; central splotch on banner petal, 73A; towards the base, 57C; at the base, 57A. Fully opened, lower surface: 73C to 73D; thin central stripe, 74A.

*Sepals.*—Quantity/arrangement: Three; one modified into an elongated spur. Length: About 1.1 cm. Width: About 5 mm. Shape: Elliptical. Apex: Acuminate. Base: Obtuse. Margin: Entire. Texture, upper and lower surfaces: Smooth, glabrous. Color, upper surface: 59A. Color, lower surface: 63C. Spur length: About 4.5 cm. Spur diameter: At flower, about 2.5 mm; at apex, less than 1 mm. Spur texture: Smooth, glabrous. Spur color: 60A to 60B.

*Peduncles.*—Length: About 4.2 cm. Diameter: About 1.5 mm. Angle: About 30° to 45° from vertical. Strength: Strong. Texture: Smooth, glabrous. Color: 60B.

*Reproductive organs.*—Stamens: Quantity: Five fused at anthers; filaments free. Anther size: About 3 mm by 4 mm. Anther color: 160D. Pollen amount: Scarce. Pollen color: 158B. Pistils: Quantity per flower: One. Pistil length: About 4 mm. Stigma shape: Rounded. Stigma color: 181D. Style color: Darker than 59A. Ovary color: Darker than 59A.

*Seed/fruit.*—Seed and fruit production have not been observed.

Disease/pest resistance: Plants of the new *Impatiens* have not been observed to be resistant to pathogens and pests common to New Guinea *Impatiens*.

Temperature tolerance: Plants of the new *Impatiens* have been observed to tolerate temperatures from about 16° C. to about 30° C.

It is claimed:

1. A new and distinct New Guinea *Impatiens* plant named 'KIE186' as illustrated and described.

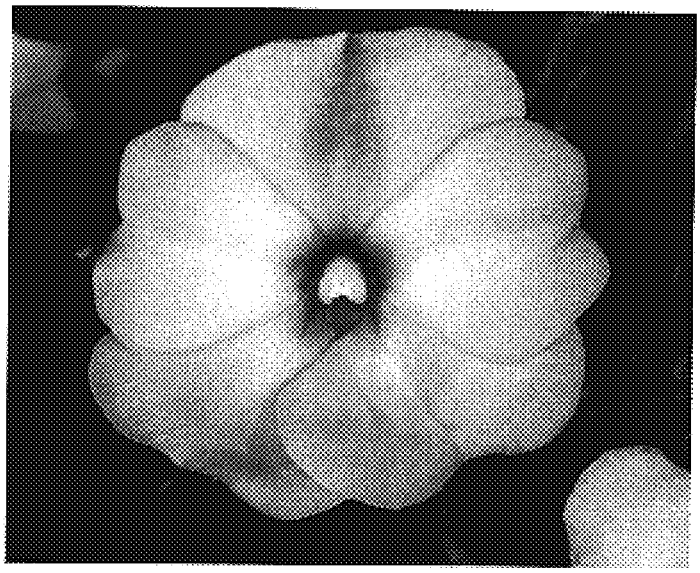
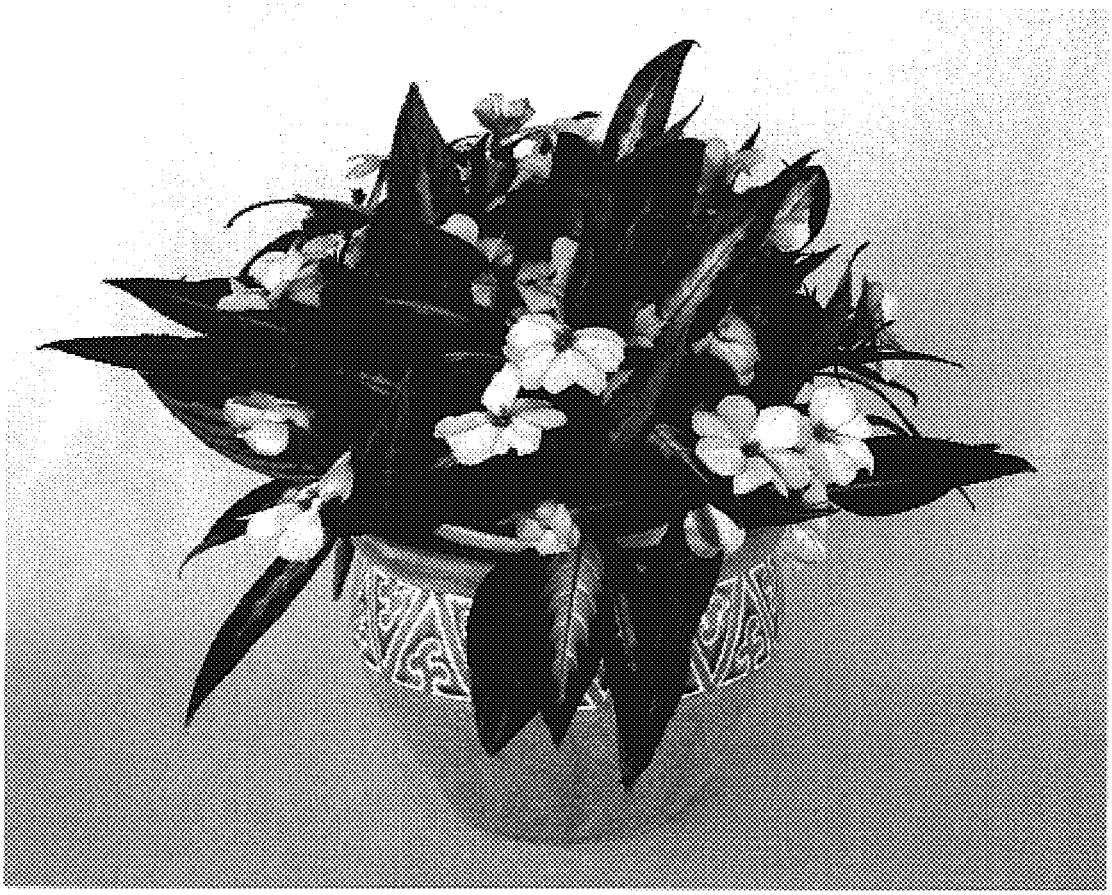

* * * * *